United States Patent [19]
Hammond et al.

[11] Patent Number: 4,734,421
[45] Date of Patent: Mar. 29, 1988

[54] ANTI-INFLAMMATORY SUBSTITUTED 2-BENZYL-MERCAPTO-IMIDAZOLE AND PYRIMIDINE DERIVATIVES COMPOSITIONS AND METHOD OF USE THEREFOR

[75] Inventors: Milton L. Hammond, Somerville; Robert A. Zambias, Springfield, both of N.J.

[73] Assignee: Merck & Co., Inc., Rahway, N.J.

[21] Appl. No.: 924,391

[22] Filed: Oct. 29, 1986

[51] Int. Cl.$^4$ ............... H61K 31/415; H61K 31/505; C07D 233/84; C07D 239/38
[52] U.S. Cl. ..................................... 514/274; 514/395; 514/397; 514/398; 514/400; 544/318; 548/327; 548/329; 548/336; 548/337
[58] Field of Search ............... 544/318; 548/327, 329, 548/336, 337; 514/274, 395, 397, 398, 400

[56] References Cited
PUBLICATIONS

March et al., Textbook "Adv. Org. Chem", 2nd Ed., McGraw-Hill, N.Y., N.Y., 1977, pp. 374, 375 and 596–598.
Shen et al., "The Development of Anti Asthmatic Drugs", Part III, Butterworth Publishers, 1983, Kent, England, 315–317 and 331–335.

*Primary Examiner*—Henry R. Jiles
*Assistant Examiner*—J. G. Mullins
*Attorney, Agent, or Firm*—Theresa Y. Cheng; Michael C. Sudol

[57] ABSTRACT

Substituted 2-benzyl-mercapto-imidazoles and analogs were prepared from the nucleophlic substitution of an appropriately substituted benzoxyacetate with a 2-imidazole mercapto anion or an analog thereof. These compounds were found to be anti-inflammatory agents.

9 Claims, No Drawings

ANTI-INFLAMMATORY SUBSTITUTED 2-BENZYL-MERCAPTO-IMIDAZOLE AND PYRIMIDINE DERIVATIVES COMPOSITIONS AND METHOD OF USE THEREFOR

BACKGROUND OF THE INVENTION

The present invention relates to novel 2-benzyl-mercapto-imidazoles and analogs useful as anti-inflammatory agents. 2-(p-nitrobenzylthio)-imidazolines (U.S. Pat. No. 3,772,440 and U.S. Pat. No. 4,146,649) have been known to have anti-parkinsonism and hypotensive activities. However, these patents did not disclose the novel compounds of the present invention, nor did they disclose the anti-inflammatory activity of these compounds.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteinases—the destructive peptide bond cleaving enzyme which has been shown to be directly involved in rheumatoid cartilage destruction; and
(2) Prostaglandins (PG) (e.g., $E_2$ and $I_2$ by mouse peritoneal macrophages) and other arachidonic acid derivatives derived from both the cyclooxygenase and the lipoxygenase pathways.

These archidonic acid oxygenation products have been identified as the critical mediators of various inflammatory conditions.

Interruption of these pathways by enzyme inhibition has been explored for effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, Science, 220, 568 (1983); D. Bailey et al. *Ann. Rpts. Med. Chem.*, 17, 203 (1982)).

Conditions involving elevated intraocular pressures which are too high for normal function may result in irreversible loss of visual function. For example, glaucoma, if untreated, may lead to ocular hypertension, inflammation, and eventually blindness.

To be an effective and acceptable topical agent, for treating inflammation in the eye, such as that caused by glaucoma or other eye diseases, the drug must not only penetrate the ophthalmic tissues to reach the active sites within the eye, but it must also be devoid of those side effects including irritation, allergic reaction and the like which would interfere with long term administration.

Pharmacological agents which are capable of inhibiting the formation of, the release of a mediator from, or the function of macrophages or polymorphonuclear leukocytes may also be effective agents in the treatment of various inflammatory conditions, e.g., pain, fever, rheumatoid arthritis, osteoarthritis, bronchial inflammation, inflammatory bowel disease, asthma, allergic disorders, skin diseases, cardiovascular disorders, glaucoma, emphysema, acute respiratory distress syndrome, spondylitis, lupus, gout, psoriasis, and other prostaglandis and/or leukotriene mediated diseases.

Accordingly, an object of this invention is to provide novel compounds as inhibitors of cyclooxygenase and lipoxygenase useful as anti-inflammatory agents.

Another object of this invention is to provide appropriate processes for the preparation of the novel compounds.

Still a further object of the present invention is to provide a pharmaceutically acceptable composition containing an effective amount of the active compound for the treatment of various inflammatory conditions.

Finally, it is the object of this invention to develop a method of treating inflammation via the administration of a therapeutically effective amount of the novel compounds a pharmaceutically acceptable composition containing one or more of these active compounds.

DETAILED DESCRIPTION OF THE INVENTION

A. Scope of the Invention

This invention relates to novel compounds of formula (I) or formula (II)

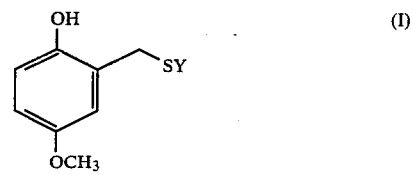

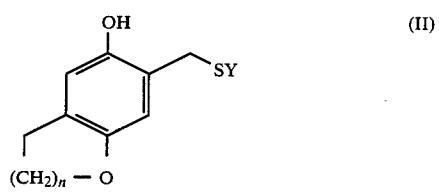

or a pharmaceutically acceptable salt thereof.
wherein
Y is

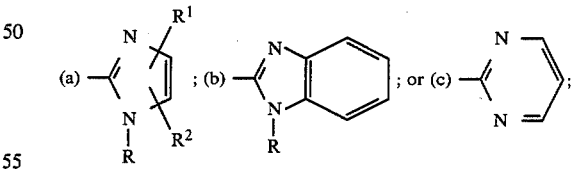

R is
(a) loweralkyl especially $C_{1-6}$ alkyl, e.g. $CH_3$, $C_2H_5$, $(CH_3)_2CH$ and butyl;
(b) lower alkanoyl especially $C_{1-6}$ alkanoyl;
(c) lowerhaloalkyl;
(d) haloloweralkanoyl especially halo $C_{1-6}$ alkanoyl such as trifluoroacetyl;
(e) H;
(f) aryl especially phenyl or phenyl substituted with one or more $R^1$ which is as defined below;
$R^1$ and $R^2$ independently are
(1) hydrogen;

(2) halo especially fluoro, chloro or bromo;
(3) loweralkoxy especially $C_{1-6}$ alkoxy, e.g., methoxy, ethoxy, isopropoxy, t-butoxy or cyclohexyloxy, or $-OCH_2O-$;
(4) lower alkylthio especially $C_{1-6}$ alkylthio, or $C_{1-6}$ haloalkylthio e.g., methylthio, ethylthio, trifluoromethylthio or cyclohexylthio;
(5) lower alkyl sulfinyl especially $C_{1-6}$ alkyl sulfinyl, e.g., methyl sulfinyl, i-propyl sulfinyl, and cyclopentyl sulfinyl;
(6) lower alkyl sulfonyl especially $C_{1-6}$ alkyl sulfonyl such as methyl sulfonyl, ethyl sulfonyl and n-butyl sulfonyl;
(7) unsubstituted or substituted phenyl loweralkoxy such as benzyloxy;
(8) loweralkyl especially $C_{1-6}$ alkyl such as methyl, ethyl, propyl, t-butyl, pentyl, benzyl, cyclopropyl, cyclopentyl or cyclohexyl;
(9) loweralkenyl especially $C_{2-6}$ alkenyl, for example, vinyl, allyl, and buten-2-yl;
(10) lower alkanoyl especially $C_{1-6}$ alkanoyl such as formyl, acetyl or i-propanoyl;
(11) haloloweralkyl especially $C_{1-6}$ haloalkyl such as trifluoromethyl;
(12) —COOH;
(13) aryl especially phenyl or substituted phenyl, e.g., 4-methoxyphenyl, 2,4-difluorophenyl or 3-chlorophenyl; or
(14) aryloxy especially phenoxy;
(15) cyano;
(16) hydroxyloweralkyl especially hydroxy $C_{1-3}$alkyl such as —$CH_2OH$;
(17) halo loweralkanoyl especially halo$C_{1-6}$ alkanoyl eq. $CF_3CO$;
(18) loweralkanoyloxy especially acetyloxy; and n is 1 or 2.

In a preferred embodiment of this invention, the compounds are of formula (I) wherein
R is
 (a) H;
 (b) $C_{1-6}$alkyl;
 (c) phenyl or substituted phenyl; and
$R^1$ is
 (a) H;
 (b) $C_{1-6}$alkyl;
 (c) phenyl;

In a more preferred embodiment of this invention, the compounds are of formula (I) wherein
R is
 (a) hydrogen;
 (b) $CH_3$ or t-butyl; or
 (c) phenyl; and
$R^1$ is
 (a) H;
 (b) $CH_3$; or
 (c) phenyl.

B. Preparation of the Compounds within the Scope of the Invention

The novel compounds of the present invention are prepared from the following process, for example,

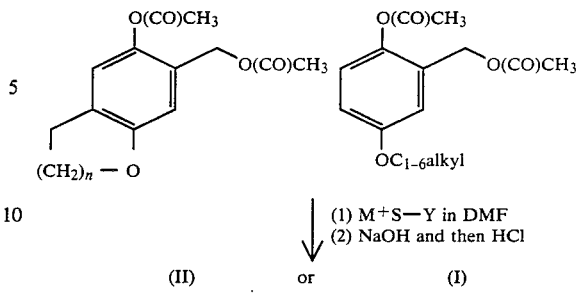

(II)    or    (I)

wherein $M^+$ is $K^+$, $Na^+$ or $Li^+$

C. Utility of the Subject Compounds of the Invention

This invention also relates to a method of treating inflammation in patients in need of such treatment. Generally, a sufficient amount of a compound of formula (I) or a pharmaceutical composition thereof, particularly an especially preferred compound, is administered to the patient as the active constituent.

The rat foot edema assay CFE and the topical mouse ear assay were used to evaluate the anti-inflammatory activity of the novel compounds of the present invention. These are established assay for screening non steroridal anti-inflammatory agents.

A. Topical Mouse Ear Assay

The right ears of mice (5 mice per group) were treated topically with either 5μ PMA (polymorphonuclear leukocytes) or 1000μ AA alone or with the test compound in 25μ of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by cervical dislocation and a 6 mm diameter disc of tissue punched from both the treated and untreated ears. The tissue biopsies were immediately weighed and the weight increase of the treated ear relative to the weight of the untreated ear determined.

Results: The effect of representative compounds on Mouse Ear Edema

TABLE 1

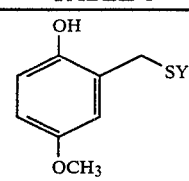

| Y | Dosage (μg) | Edema (% inhibition) |
|---|---|---|
| ![pyrazole N-CH3] | 300 | 45 |
| ![imidazole N-CH3, CH3] | 300 | 65 |

TABLE 1-continued

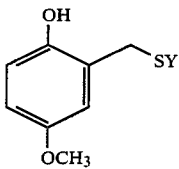

| Y | Dosage (μg) | Edema (% inhibition) |
|---|---|---|
| 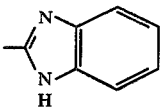 | 300 | 76 |
| 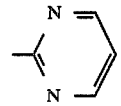 | 300 | 32 |

B. Rat Foot Edema Assay (CFE)

Representative compounds of formula (I) or (II) were tested according to the well-established procedures of rat foot edema assay published in 1962 by C. A. Winter, E. A. Risley and G. W. Nuss, *Proc Soc Exp Biol Med.* III, 544 (1962).

Results: The effect of representative compounds on Rat Foot Edema

TABLE 2a

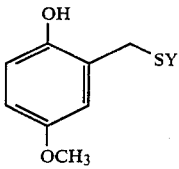

| Y | Dosage (μg) | Edema (% inhibition) |
|---|---|---|
| 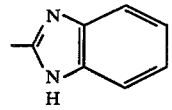 | 30 | 74 |
| 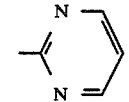 | 30 | 54 |
| 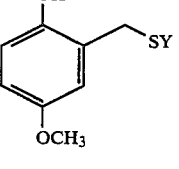 | 30 | 77 |
| 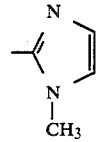 | 30 | 74 |

TABLE 2a-continued

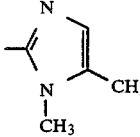

| Y | Dosage (μg) | Edema (% inhibition) |
|---|---|---|
| 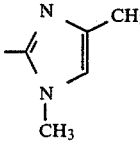 | 30 | 21 |
| 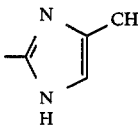 | 30 | 3 |

TABLE 2b

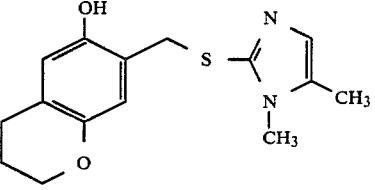

| Dosage (mpk) | % Inhibition |
|---|---|
| 30 | 42 |

For the treatment of inflammation, arthritis conditions, cardiovascular disorder, allergy, psoriasis, asthma, or other diseases mediated by prostaglandins and/or leukotrienes, a compound of Formula (I) may be administered systemically (orally or parenterally) or topically, in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques.

Pharmaceutical compositions containing the active ingredient may be in a form of tablets, capsules, aqueous or oily solutions or suspensions, dispersible powders or granules, tinctures, topical aerosol emulsions, creams, ointments, jellies, suppositories or the like. These compositions may be prepared according to any method known to the art for the manufacture of pharmaceutical compositions and such compositions may contain one or more active compounds.

When given systemically, the drug can be given by any route, although the oral route is preferred. In oral administration the drug can be employed in any of the usual dosage forms such as tablets, capsules, solutions, suspensions, or powders, either in a contemporaneous delivery or sustained release form. Any number of the usual excipients or tableting aids can likewise be included.

When given by the topical route, the active drug or a pharmaceutically acceptable salt thereof such as the sodium or potassium salt is formulated into a topical preparation, for example, solutions, suspensions, powders, tinctures, aerosol emulsions, creams, ointments, sprays, jellies or suppositories.

Dosage levels of the order to 0.2 mg to 140 mg per kilogram of body weight per day are useful in the treatment of the above-indicated conditions (10 mg to 7 gms per patient per day). For example, inflammation may be effectively treated by the administration from about 0.5 to 50 mg of the compound per kilogram of body weight per day (25 mg to 5 gms per patient per day). Advantageously, from about 2 mg to about 20 mg per kilogram of body weight per daily dosage produces highly effective results (50 mg to 1 gm per patient per day).

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

2-(((1,4-Dimethyl-1H-imidazole-2-yl)thio)methyl)-4-methoxyphenolyl

To a solution of potassium hydroxide (7.54 g, 134 mmal) in absolute ethanol (500 ml) was added 1,4-dimethylimidazole-2-thiol(14.4 g, 112 mmol). The solution of the potassium salt was concentrated to dryness, taken up in dry dimethylformamide (100 ml) and added to a solution of 2-hydroxymethyl-4-methoxyphenol diacetate (27.7 g, 116 mmal) in dimethylformamide (125 ml). The mixture was allowed to stir at room temperature for ninety minutes, then worked up by pouring into water (800 ml) and basifying with 2.5N sodium hydroxide (45 ml). The suponification was allowed to proceed for ten minutes, then diluted with water (1000 ml) and adjusted to pH 8 with 3N hydrochlorine acid. The aqueous mixture was extracted with ethyl acetate (4×400 ml), and the combined extracts were dried (Na$_2$SO$_4$) and concentrated. Chromatography over silica (2:1 hexane:ethyl acetate as elevant) afforded 2-(((1,4-dimethyl-1H-imidazole-2-yl)thio)methyl-4-methoxyphenol (15.7 g, 53%). Recrystallization from hexane/methylene chloride afforded the pure product, mp 111°-112° C.

EXAMPLE 2

In an analogous manner to that described in Example 1, 4(5)-methylimidazole-2-thione (2.45 g, 21.5 mmal) was converted to 2-((4-methyl-1H-imidazole-2-yl)thio)-methyl-4-methoxyphenol (0.39 g, 7%) mp 116°-118° C.

EXAMPLE 3

In an analogous manner to that described in Example 1, 1,5-dimethylimidazole-2-thione (2.77 g, 21.6 mmal) was converted to 2-(((1,5-dimethyl-1H-imidazole-2-yl)thio)methyl-4-methoxyphenol (2.10 g, 37%) mp 121°-122° C.

EXAMPLE 4

In an analogous manner to that described in Example 1, 1-methyl-4-phenylimidazole-2-thione (3.32 g, 17.5 mmal) was converted to 2-(((1-methyl-4-phenyl-1H-imidazole-2yl)thio)methyl)-4methoxyphenyl (2.4 g, 42%) mp 140°-141.5° C.

EXAMPLE 5

In an analogous manner to that described in Example 1, 1-methyl-4-((1,1-dimethylethyl)-imidazole-2-thione (1.85 g, 10.9 mmal) was converted to 2-(((1-methyl-4-((1,1-dimethylethyl)-1H-imidazole-2-yl)thio)methyl)-4-methoxyphenyl (1.7 g, 51%). mp 154°-156° C.

EXAMPLE 6

In an analogous manner to that described in Example 1, 1-phenyl-4-methylimidazole-2-thione (2.06 g, 10.9 mmal) was converted to 2-(((1-phenyl-4-methyl-1H-imidazole-2-yl)thio)methyl)-4-methoxyphenyl (290 mg, 8%). mp 90°-92° C.

EXAMPLE 7

In an analogous manner to that described in Example 1, 4,5-di-phenylimidazole-2-thione (8.07 g, 32.0 mmal) was converted to 2-(((4,5-diphenyl-1H-imidazole-2-yl)thio)methyl)-4-methoxyphenyl (3.50 g, 28%). mp 184°-186° C.

EXAMPLE 8

In an analogous manner to that described in Example 1, 1-methyl-5-phenylimidazole-2-thione (1.55 g, 8.2 mmal) was converted to 2-(((1-methyl-5-phenyl-1H-imidazole-2-yl)thio)methyl)-4-methoxyphenyl (830 mg, 32%).

EXAMPLE 9

In an analogous manner to that described in Example 1, benzimidazole-2-thione (3.04 g, 20.3 mmal) was converted to 2-(((1H-benzimidazole-2-yl)thio)methyl)-4-methoxyphenyl (2.5 g, 43%). mp 161°-164° C.

EXAMPLE 10

In a manner analogous to Example 1, 1,5-dimethylimidazole-2-thione (0.80 g, 6.25 mmal) was treated with 6-hydroxy-7-hydroxymethyl-1,2,3,4-tetrahydrobenzopyran diacetate (1.70 g, 6.25 mmal) to afford 7-(((1,5-dimethyl-1H-imidazole-2-yl)thio)methyl)-6-hydroxy-1,2,3,4-tetrahydrobenzopyran (480 mg, 26%) mp 139°-140° C.

EXAMPLE 11

In an analogous manner to Example 1, pyrimidine-2-thiol (3.0 g, 26.7 mmal) was converted to 2-(((pyrimidine-2-yl)thio)methyl)-4-methoxyphenyl (900 mg, 13%), mp 67° C.

What is claimed is:

1. A compound of formula (I)

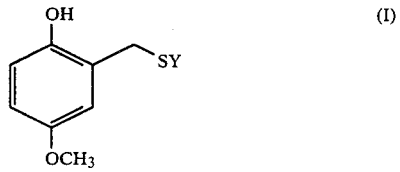

or a pharmaceutically acceptable salt thereof wherein

Y is

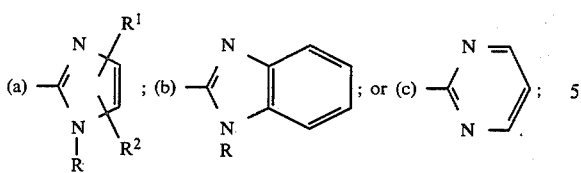

R is
- (a) H;
- (b) C$_{1-6}$alkyl;
- (c) phenyl or phenyl or substituted with one or more substituents selected from a group consisting of
  - (1) hydrogen;
  - (2) halo;
  - (3) loweralkoxy;
  - (4) loweralkylthio;
  - (5) loweralkylsulfinyl;
  - (6) loweralkylsulfonyl;
  - (7) loweralkyl;
  - (8) loweralkanoyl;
  - (9) haloloweralkyl;
  - (10) —COOH;
  - (11) hydroxyloweralkyl;
  - (12) halo loweralkyanoyl; or
  - (13) loweralkanoyloxy;

R$^1$ and R$^2$ independently are
- (a) H;
- (b) C$_{1-6}$alkyl; or
- (c) phenyl.

2. The compound of formula (I) according to claim 1 wherein:

R is
- (a) hydrogen; or
- (b) CH$_3$ or t-butyl; and

R$^1$ and R$^2$ are
- (a) H; or
- (b) CH$_3$.

3. The compound of claim 1 which is of formula

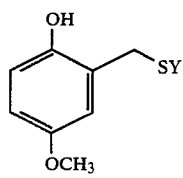

wherein
- (a) Y is 2-(1-methylimidazolyl);
- (b) Y is 2-(1,3-dimethylimidazolyl);
- (c) Y is 2-benzoimidazolyl;
- (d) Y is 2-(1,5-dimethylimidazolyl);
- (e) Y is 2-(4-methylimidazolyl); or
- (f) Y is

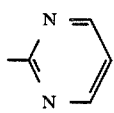

4. A pharmaceutical composition for treating topical inflammation comprising a pharmaceutical carrier and an antiinflammatory effective amount of a compound of formula (I)

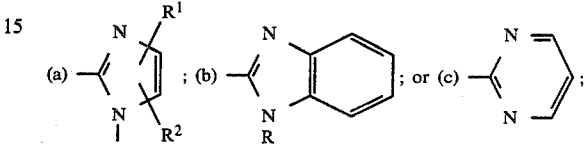

or a pharmaceutically acceptable salt thereof
wherein
Y is

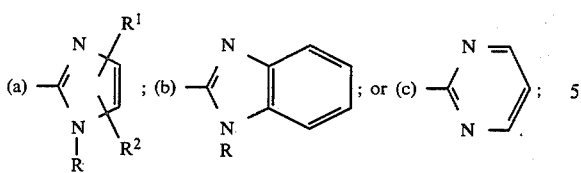

R is
- (a) H;
- (b) C$_{1-6}$alkyl;
- (c) phenyl or substituted phenyl with one or more substituents selected from a group consisting of
  - (1) hydrogen;
  - (2) halo;
  - (3) loweralkoxy;
  - (4) loweralkylthio;
  - (5) loweralkylsulfinyl;
  - (6) loweralkylsulfonyl;
  - (7) loweralkyl;
  - (8) loweralkanoyl;
  - (9) haloloweralkyl;
  - (10) —COOH;
  - (11) hydroxyloweralkyl;
  - (12) halo loweralkyanoyl; or
  - (13) loweralkanoyloxy;

R$^1$ and R$^2$ independently are
- (a) H;
- (b) C$_{1-6}$alkyl; or
- (c) phenyl.

5. The pharmaceutical composition of claim 4 wherein the compound is of formula (I);

R is
- (a) hydrogen; or
- (b) CH$_3$ or t-butyl; and

R$^1$ and R$^2$ independently are
- (a) H; or
- (b) CH$_3$.

6. The pharmaceutical composition of claim 4 wherein the active compound is

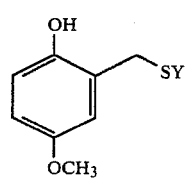

wherein
- (a) Y is 2-(1-methylimidazolyl);
- (b) Y is 2-(1,3-dimethylimidazolyl);
- (c) Y is 2-benzoimidazolyl;
- (d) Y is 2-(1,5-dimethylimidazolyl);
- (e) Y is 2-(4-methylimidazolyl); or (f) Y is

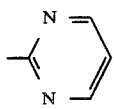

7. A method of treating or decreasing topical inflammation comprising the administration to a mammalian species in need of such treatment an antiinflammatory amount of a compound of formula (I)

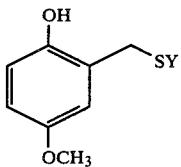 (I)

or a pharmaceutically acceptable salt thereof wherein
Y is

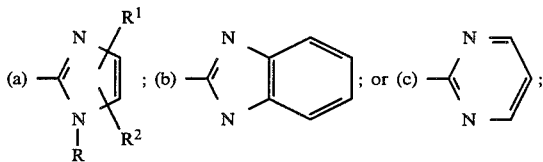

R is
(a) H;
(b) $C_{1-6}$alkyl;
(c) phenyl or substituted phenyl with one or more substituents selected from a group consisting of
(1) hydrogen;
(2) halo;
(3) loweralkoxy;
(4) loweralkylthio;
(5) loweralkylsulfinyl;
(6) loweralkylsulfonyl;
(7) loweralkyl;
(8) loweralkanoyl;
(9) haloloweralkyl;
(10) —COOH;
(11) hydroxyloweralkyl;
(12) halo loweralkyanoyl; or
(13) loweralkanoyloxy;

$R^1$ and $R^2$ independently are
(a) H;
(b) $C_{1-6}$alkyl; or
(c) phenyl.

8. The method of claim 7 wherein the compound is of formula (I);
R is
(a) hydrogen; or
(b) $CH_3$ or t-butyl; and
$R^1$ and $R^2$ independently are
(a) H; or
(b) $CH_3$.

9. The method of claim 7 wherein the compound is:

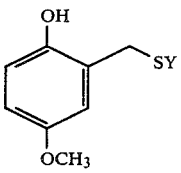

wherein
(a) Y is 2-(1-methylimidazolyl);
(b) Y is 2-(1,3-dimethylimidazolyl);
(c) Y is 2-benzoimidazolyl;
(d) Y is 2-(1,5-dimethylimidazolyl);
(e) Y is 2-(4-methylimidazolyl); or
(f) Y is

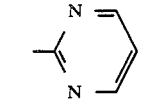

* * * * *